US006444853B1

(12) United States Patent
Arai et al.

(10) Patent No.: US 6,444,853 B1
(45) Date of Patent: Sep. 3, 2002

(54) PROCESS FOR PRODUCING AROMATIC DISULFIDES

(75) Inventors: Isamu Arai; Tutomu Yamaguchi; Yoko Hida, all of Toda (JP)

(73) Assignee: Nippon Finechemical Co., Ltd., Tokyo (JP)

(*) Notice: Subject to any disclaimer, the term of this patent is extended or adjusted under 35 U.S.C. 154(b) by 0 days.

(21) Appl. No.: 09/806,850

(22) PCT Filed: Aug. 12, 1999

(86) PCT No.: PCT/JP99/04371

§ 371 (c)(1),
(2), (4) Date: Apr. 4, 2001

(87) PCT Pub. No.: WO01/12595

PCT Pub. Date: Feb. 22, 2001

(51) Int. Cl.$^7$ ............................................. C07C 321/24
(52) U.S. Cl. ........................................... 568/23; 568/24
(58) Field of Search .............................. 568/21, 23, 24, 568/25, 36, 37

(56) References Cited

U.S. PATENT DOCUMENTS 3,235,597 A    2/1966   Mills et al.
5,998,670 A  * 12/1999   Tang et al. ................... 568/26

FOREIGN PATENT DOCUMENTS

| JP | 44-26100 | 11/1969 |
| JP | 02-295968 A | 12/1990 |
| JP | 08-143533 A | 6/1996 |
| JP | 10-45706 A | 2/1998 |

OTHER PUBLICATIONS

CA:112:197728 abs of Sulfur Lett. by Aliev et al 9(4) pp159–66 1989.*
CA:128:140734 abs of JP10045706 1998.*
Y. Takigawa, "Synthesis of mercaptans by sodium hydrogen sulfide–liquid ammonia solution", Kogyo Kagaku Zasshi, vol. 70, pp. 114–118 (1967), **English–language abstract attached.

D.A. Dickman et al, "Oxidative Cleavage of Aryl or Alkyl tert–Butyl Sulfides with Dimethyl Sulfoxide/Hydrobromic Acid to Form Symmetrical Aryl of Alkyl Disulfides", Journal of Synthetic Organic Chemistry, *Synthesis*, No. 6, pp. 573–574 (1993).

* cited by examiner

*Primary Examiner*—Jean F. Vollano
(74) *Attorney, Agent, or Firm*—Frishauf, Holtz, Goodman & Chick, P.C.

(57) ABSTRACT

This invention relates to a process for the preparation of aromatic disulfides represented by the formula (II):

$$Y_n\text{—Ar—S—S—Ar—}Y_n \qquad \text{(II)}$$

wherein Ar represents a hydrocarbon aromatic ring group; Y represents a monovalent electrophilic group, and when n is 2 or more, a plural number of Y's may be the same or different from each other; and n is an integer of 1 to 12, which comprises allowing (A) an aromatic thioether represented by the formula (I):

$$Y_n\text{—Ar—S—R} \qquad \text{(I)}$$

wherein Y, Ar and n have the same meanings as defined above; and R represents a monovalent hydrocarbyl group selected from the group consisting of a monovalent tertiary hydrocarbyl group, and benzyl group and a monovalent secondary hydrocarbyl group derived from benzyl group;

to react with (B) at least one of the following (1) to (4):
 (1) bromine;
 (2)(a) hydrogen bromide and (b) hydrogen peroxide;
 (3)(c) chlorine, in the presence of a catalytic amount of iodine and/or hydrogen iodide;
 (4)(d) hydrogen chloride and (b) hydrogen peroxide, in the presence of a catalytic amount of iodine and/or hydrogen iodide.

28 Claims, No Drawings

PROCESS FOR PRODUCING AROMATIC DISULFIDES

This application is the national phase application of International Application PCT/JP99/04371 (not published in English) filed Aug. 12, 1999.

TECHNICAL FIELD

This invention relates to a process for the preparation of aromatic disulfides from aromatic thioethers, more specifically, to a process for the preparation of aromatic disulfides which comprises reacting aromatic thioether and halogen or precursor thereof.

BACKGROUND ART

Aromatic disulfides having an electrophilic group bonded to an aromatic ring, particularly aromatic disulfides represented by the general formula (II'):

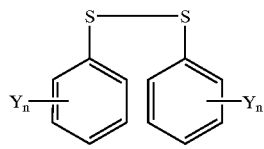

(II')

wherein Y represents a monovalent electrophilic group which may be the same or different from each other; and n is an integer of 1 to 5, have been widely-used as intermediates of medicines and agricultural chemicals.

Aromatic disulfides having such a substituent can be usually produced by the oxidation of corresponding aromatic thiols. As a process for the preparation of said aromatic thiols, several processes have been proposed.

For example, there have been proposed a method of mercaptization of a polychlorinated benzene by sodium sulfide dissolved in liquid ammonia in an autoclave (Kogyo Kagaku Zasshi, vol. 70, pp. 114–118 (1967)); a method for the preparation of halogenated aromatic thiols by reacting sodium nitrite with an amino group-containing aromatic halide to obtain a diazonium salt, followed by reacting it with potassium O-ethyldithio-carbonate and treating the same with an alkali (Japanese Patent Publication No. 26100/1969); a method for the preparation of halogenated thiophenols by the reduction of 4-halobenzensulfinic acids in the presence of a mineral acid and zinc powder (Japanese Provisional Patent Publication No. 295968/1990), etc.

However, these methods are limited since high pressure reaction using liquid ammonia shall be carried out, they are dangerous since diazonium salts are formed, and require a specific apparatus for carrying out the reduction in the presence of a mineral acid, etc., and in either of these methods, yields are low and the purification of the desired product is difficult.

Moreover, in Japanese Provisional Patent Publication No. 143533/1996, a method for the preparation of aromatic thiols by the chlorination of a methyl group bonded to a sulfur atom of thioanisol with a chlorine gas and then hydrolysis of the resulting compound in the presence of a mineral acid has been disclosed. However, in this method, methyl mercaptane, which is volatile and stinking, must be used and complex steps to introduce chlorine gas are required for the chlorination of the methyl group.

Desired aromatic disulfides can be obtained by the oxidation and the dimerization of the aromatic thiols obtained by these methods with an oxidizing agent. However, according to these methods, multi-step reactions in which aromatic thiols are once obtained and then aromatic disulfides are formed by the dimerization reaction shall be carried out. Also, most of the aromatic thiols are sublimable so that the drying and the purification become complex and they have irritating property whereby they should be handled carefully. Accordingly, it is earnestly desired to obtain a process for the preparation of aromatic disulfides without passing through aromatic thiols.

In Synthesis, June, 1993, pp. 573–574 (written by D. A. Dickman et al.), a method for the preparation of disulfides represented by the formula:

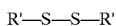

wherein R' represents a phenyl group which is unsubstituted or substituted by a formyl group, a benzyl group or a n-butyl group, by the reaction of a thioether represented by the formula:

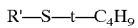

wherein R' has the same meaning as defined above, with an acetic acid solution of hydrobromic acid in the presence of dimethylsulfoxide. However, according to this method, dimethylsulfide having remarkably bad smell is formed by the reaction of dimethylsulfoxide so that recovery of the same shall be carried out without dissipating it in air. Also, depending on the kind of R', the reaction does not substantially proceed under the conditions disclosed therein and no desired compound can be obtained.

DISCLOSURE OF THE INVENTION

An object of this invention is to produce aromatic disulfides having an electrophilic group from aromatic thioether which can be relatively easily synthesized with a simple and easy method, with good purity and without generating byproducts handling of which are complicated.

The present inventors have earnestly studied to solve the above-mentioned problems, and as a result, they have found that the above objects can be accomplished by the reaction of an aromatic thioether having a hydrocarbyl group and a substituted aromatic ring with halogen such as bromine, and found that the same results can be obtained when hydrogen halide and hydrogen peroxide are used as precursors of said halogen to accomplish this invention.

That is, this invention relates to a process for the preparation of aromatic disulfides represented by the formula (II):

(II)

wherein Ar represents a hydrocarbon aromatic ring group;
Y represents a monovalent electrophilic group, and when n is 2 or more, a plural number of Y's may be the same or different from each other; and n is an integer of 1 to 12, which comprises allowing (A) an aromatic thioether represented by the formula (I):

(I)

wherein Y, Ar and n have the same meanings as defined above; and R represents a monovalent hydrocarbyl group selected from the group consisting of a monovalent tertiary hydrocarbyl group, and a benzyl group and a monovalent secondary hydrocarbyl group derived from a benzyl group;
to react with
(B) at least one of the following (1) to (4):
(1) bromine;
(2)(a) hydrogen bromide and (b) hydrogen peroxide;
(3)(c) chlorine, in the presence of a catalytic amount of iodine and/or hydrogen iodide;
(4)(d) hydrogen chloride and (b) hydrogen peroxide, in the presence of a catalytic amount of iodine and/or hydrogen iodide.

EMBODIMENTS FOR CARRYING OUT THE INVENTION

When the preparation process of this invention is shown by a chemical formula, it become as follows:

$$2Y_n-Ar-S-R+X_2 \rightarrow Y_n-Ar-S-S-Ar-Y_n+2RX$$

wherein X is a halogen atom, and Ar, R, Y and n have the same meanings as defined above.

(A) an aromatic thioether to be used in this invention is thioether derivatives having one —SR bonded to the carbon atom of the aromatic ring, and having at least one of Y.

Ar is a hydrocarbon aromatic group. As Ar, there may be mentioned an aromatic group such as benzene, biphenyl, terphenyl, naphthalene, anthracene, pyrene rings, etc. A benzene ring group is particularly preferred due to the reactivity with (B) and usefulness of the resulting disulfides.

Y is a monovalent electrophilic group which is bonded to a carbon atom of the aromatic ring group Ar, and introduced as a substituent into the aromatic disulfides which are objective products. According to the presence of Y. the reaction of (A) and (B) is promoted and a substitution reaction of a hydrogen atom on the aromatic ring with halogen can be restrained. As Y, there maybe typically mentioned halogenated, nitro, nitrile, sulfone, sulfamoyl or hydrocarbylsulfonyl groups. As the halogenated, there may be mentioned fluoro, chloro, bromo and iodo, and as the hydrocarbylsulfonyl group, there may be mentioned methylsulfonyl, phenylsulfonyl, p-toluylsulfonyl, etc. When a plural number of Y's exist, they may be the same or different from each other.

n is an integer of 1 to 12, and, for example, when Ar is a benzene ring group, it is an integer of 1 to 5, and when it is a terphenyl ring group, it is an integer of 1 to 12. With regard to the same Y's, the larger the n is, the easier the reaction of (A) and (B) proceeds.

R is a monovalent hydrocarbyl group within a specific range, which binds to a sulfur atom, and more specifically, it is selected from a monovalent tertiary hydrocarbyl group, and a benzyl group and a monovalent secondary hydrocarbyl group derived from the benzyl group. As the tertiary hydrocarbyl groups, there may be exemplified by tertiary alkyl groups such as t-butyl, t-pentyl, t-hexyl, t-octyl, t-decyl, t-dodecyl, 1-methyl-1-ethylpropyl, 1,1-diethylpropyl, 1,1,4-trimethyl-pentyl, etc.; and aromatic ring-containing tertiary hydro-carbyl groups such as 1-methyl-1-phenylethyl, 1,1-diphenyl-ethyl, trityl, etc.; and as the benzyl group and a secondary hydrocarbon group derived from the benzyl group, there may be exemplified by benzyl, 1-methylbenzyl, 1-ethylbenzyl, 1-propylbenzyl, benzhydryl, etc. Of these, t-butyl, benzyl and benzhydryl are preferred since R is easily split off to form aromatic disulfides and handling thereof is easy, and t-butyl is particularly preferred.

In this invention, it is particularly preferred that 3,5-dichlorophenyl-t-butyl thioether is used as (A) to obtain bis(3,5-dichlorophenyl)disulfide since the reaction proceeds easily, and advantageous as compared with the other methods and utilities of the products are high.

(B) to be used in this invention is a reaction agent by reacting with (A) to obtain an aromatic disulfide. As the (B), at least one of the following (1) to (4) is used.

(1) is bromine. Said bromine can be introduced in the reaction system by an optional means such as dropwise addition into the reaction system by using a separating funnel. An amount of (1) is usually in the range of 0.5 to 5 mol based on 1 mol of (A) the aromatic thioether, and preferably 1 to 3 mol to effectively accelerate the reaction.

(2) is a combination of (a) hydrogen bromide which is a precursor of (1) and (b) hydrogen peroxide, and forms bromine in the reaction system. Said bromine reacts with (A) to form aromatic disulfides. (a) may be introduced in the reaction system in an anhydrous state or may be used in the form of an aqueous solution such as hydrobromic acid. When it is present in the form of an aqueous solution in the reaction system, it is preferred since handling is easy. (b) is usually employed as an aqueous solution in an amount of 10 to 50% by weight and preferably added dropwise to the reaction system so that bromine is gradually generated in the reaction system. An amount of (a) is usually in the range of 1 to 10 mol, preferably 2 to 5 mol per mol of (A). On the other hand, an amount of (b) is usually in the range of 0.5 to 5 mol, preferably 1 to 3 mol per mol of (A).

(3) is (c) chlorine and reacted with (A) in the presence of iodine and/or hydrogen iodide which contribute to as a catalyst for promoting the reaction with (A). (c) has an extremely slow reaction rate to form aromatic disulfides when it is used alone and in the presence of the above-mentioned catalyst(s), aromatic disulfides can be firstly obtained with satisfiable reaction rates. (c) can be introduced into the reaction system in optional manners, e.g., by introducing it in a gaseous state, etc. An amount of (c) is usually in the range of 0.5 to 5 mol, preferably 1 to 3 mol per mol of (A). On the other hand, an amount of the catalyst is usually in the range of 0.01 to 0.1 mol, preferably 0.02 to 0.05 mol when iodine is used as said catalyst, and is usually in the range of 0.02 to 0.2 mol, preferably 0.04 to 0.1 mol when hydrogen iodide is used.

(4) is a combination of (d) hydrogen chloride which is a precursor of (3) and (b) hydrogen peroxide which is the same as used in (2). The reaction is carried out in the presence of the same catalyst as used in (3). In the case of (d), aromatic disulfides cannot be obtained with a satisfiable reaction rate when it is used simply with (b) in combination, and the aromatic disulfides can be firstly obtained in the presence of the catalyst with a satisfiable reaction rate. The reaction can be carried out in the same manner as in the method of (2). An amount of (d) is usually in the range of 1 to 10 mol, preferably 2 to 5 mol per mol of (A). An amount of (b) is the same as in the case of the combination of (2), and an amount of the catalyst is the same as in the case of the combination of (3).

As (B), a bromine system is preferably used as in (1) or (2) since the desired aromatic disulfides can be obtained with excellent yields and good purities. On the other hand, it is preferred to use the combination of (2) or (4) due to easiness in handling thereof, so that (2) is particularly preferred in total.

The reaction is preferably carried out in the presence of an organic solvent which forms an organic phase separating from an aqueous phase. For example, where (2) or (4) is used as (B), when (a) hydrogen bromide or (c) hydrogen chloride and a catalyst is/are added to (A) dissolved in an organic solvent, and an aqueous solution of hydrogen peroxide is added dropwise to the mixture, the generated halogen dissolves in an organic phase to react with (A).

As the organic solvent, there may be exemplified by halogenated hydrocarbons such as methylene chloride, chloroform, carbon tetrachloride, chlorobenzene, etc.; aliphatic hydrocarbons such as pentane, hexane, cyclohexane, etc.; and aromatic hydrocarbons such as toluene, xylene, etc. When hydrocarbons are to be used, halogenation of hydrocarbons occurs as a side reaction(s) when light is not shielded so that halogenated hydrocarbons are preferably used.

An amount of the organic solvent is usually 50 to 1,000 parts by weight, preferably 100 to 500 parts by weight based on 100 parts by weight of (A) the aromatic thioethers.

A reaction temperature is preferably −30 to 60° C., and more preferably −10 to 30° C. since side reactions can be restrained to give aromatic disulfides with good yields.

The aromatic disulfides obtained by the reaction can be treated, for example, by collecting an organic phase separating from the system and, after washing with an aqueous solution of reductive substances such as sodium thiosulfate, etc., removing the solvent to give a purified product by means of recrystallization.

According to this invention, from aromatic thioethers having an electrophilic group at the aromatic ring, corresponding aromatic disulfides can be obtained with one step reaction directly with excellent yields and high purities without formation of a product(s) recovery of which is/are complex such as dimethylsulfide, etc. The process of this invention is particularly useful for the preparation of di-substituted disulfides which could not be obtained by the other methods.

The aromatic disulfides obtained by this invention are useful as intermediates for medicines, agricultural chemicals, etc.

In the following, this invention will be explained in more detail by referring to Examples. In the Examples, parts represent part by weight and % in the composition represents % by weight. In the following reaction formulae, t-Bu means a t-butyl group, Bzl a benzyl group and DMSO dimethylsulfoxide.

This invention is not limited by these Examples.

EXAMPLE 1

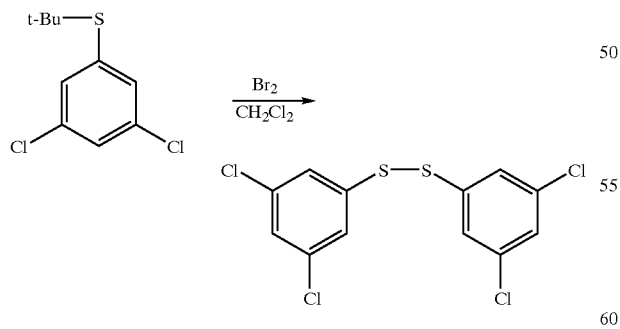

In a reaction vessel equipped with a stirrer, a thermometer and a dropping funnel were charged 13.3 parts of methylene chloride and 4.70 parts of 3,5-dichlorophenyl t-butylsulfide. Under stirring, 3.20 parts of bromine was added dropwise to the mixture over 10 minutes while maintaining the liquid temperature to 10° C., then, the reaction rapidly completed.

After completion of the reaction, methylene chloride was removed from the mixture by distillation under reduced pressure and the product was evaporated to dryness. The group was recrystallized from acetone-methanol and 2.93 parts of colorless needle crystals were obtained.

Melting point: 65° C.; $^1$H-NMR (CDCl$_3$): δ 7.33 (d, J=1.7 Hz, 4H), 7.23 (t, J=1.7 Hz, 2H).

From the results, the resulting product was confirmed to be bis(3,5-dichlorophenyl)disulfide. The yield was 82% based on the theoretical amount.

EXAMPLE 2

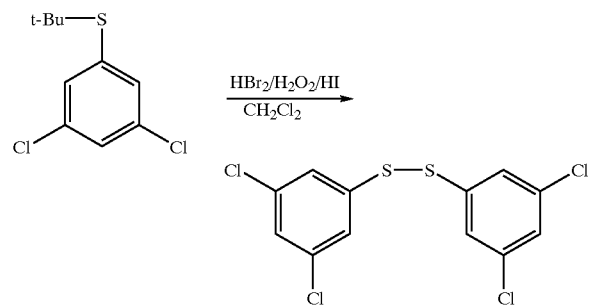

In a reaction vessel equipped with a stirrer, a thermometer and a dropping funnel were charged 66.7 parts of methylene chloride, 23.5 parts of 3,5-dichlorophenyl t-butylsulfide and 50.5 parts of 48% hydrobromic acid. Under stirring, 10.0 parts of 34% hydrogen peroxide was added dropwise to the mixture over 40 minutes while maintaining the liquid temperature to 10° C. After completion of the dropwise addition, stirring was further continued for one hour to complete the reaction.

After completion of the reaction, 66.7 parts of methylene chloride was further added to the mixture and the resulting mixture was stirred. Then, the organic phase was collected by liquid separation, washed three times with 10.8 parts of an aqueous 10% sodiumthiosulfate solution, filtered and methylene chloride was removed by distillation from the filtrate under reduced pressure. The group thus obtained was recrystallized from acetone-methanol and 15.1 parts of colorless needle crystals were obtained.

Melting point: 65° C.; $^1$H-NMR (CDCl$_3$): δ 7.33 (d, J=1.7 Hz, 4H), 7.23 (t, J=1.7 Hz, 2H).

From the results, the resulting product was confirmed to be bis(3,5-dichlorophenyl)disulfide. The yield was 85% based on the theoretical amount.

EXAMPLE 3

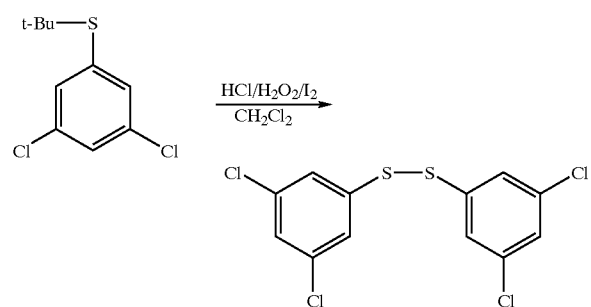

In a similar reaction vessel used in Example 1 were charged 13.3 parts of methylene chloride, 4.70 parts of 3,5-dichlorophenyl t-butylsulfide, 6.0 parts of 36% hydrochloric acid and 0.25 part of iodine. Under stirring, 2.00 parts of a 34% aqueous hydrogen peroxide solution was added dropwise to the mixture over 10 minutes while maintaining the liquid temperature to 10° C. After completion of the dropwise addition, the mixture was further stirred at the same temperature for 6 hours to complete the reaction. After completion of the reaction, purification was carried out in the same manner as in Example 2 except for changing the amount of methylene chloride added to 13.3 parts, and 2.89 parts of colorless needle crystals were obtained.

Melting point: 65° C.; $^1$H-NMR (CDCl$_3$): δ 7.33 (d, J=1.7 Hz, 4H), 7.23 (t, J=1.7 Hz, 2H).

From the results, the resulting product was confirmed to be bis(3,5-dichlorophenyl)disulfide. The yield was 81% based on the theoretical amount.

COMPARATIVE EXAMPLE 1

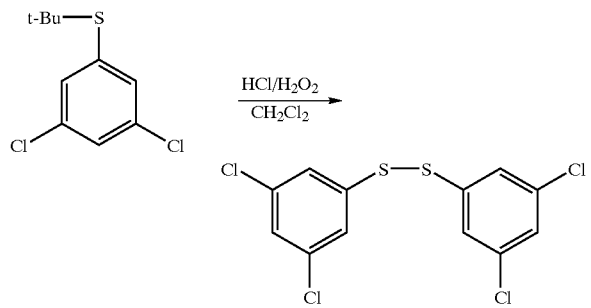

In the same manner as in Example 3 except for not using iodine, changing the amount of 36% hydrochloric acid to 12.0 parts, changing the amount of a 34% aqueous hydrogen peroxide solution to 4.04 parts and changing the dropping addition time thereof to 20 minutes, the reaction was carried out. After completion of the reaction, purification was carried out in the same manner as in Example 3 and 1.07 parts of colorless needle crystals were obtained.

Melting point: 65° C.; $^1$H-NMR (CDCl$_3$): δ 7.33 (d, J=1.7 Hz, 4H), 7.23 (t, J=1.7 Hz, 2H).

From the results, the resulting product was confirmed to be bis(3,5-dichlorophenyl)disulfide. The yield was only 30% based on the theoretical amount.

EXAMPLE 4

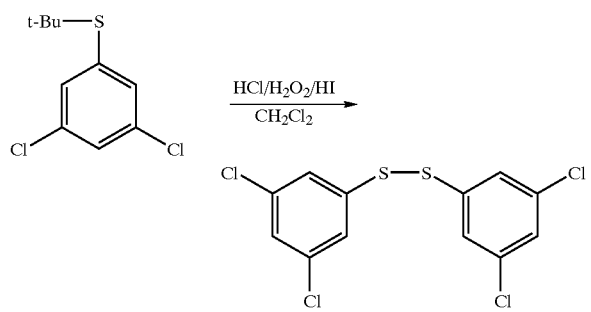

In a similar reaction vessel used in Example 1 were charged the same amounts of methylene chloride, 3,5-dichlorophenyl t-butylsulfide and 36% hydrochloric acid as in Example 3, and 0.47 part of 55% hydroiodic acid was added in place of iodine. In the same manner as in Example 3 except for changing the stirring time after addition of hydrogen peroxide to 12 hours, the reaction proceeded. After completion of the reaction, purification was carried out in the same manner as in Example 3, and 2.63 parts of colorless needle crystals were obtained.

Melting point: 650° C.; $^1$H-NMR (CDCl$_3$): δ 7.33 (d, J=1.7 Hz, 4H), 7.23 (t, J=1.7 Hz, 2H).

From the results, the resulting product was confirmed to be bis(3,5-dichlorophenyl)disulfide. The yield was 74% based on the theoretical amount.

COMPARATIVE EXAMPLE 2

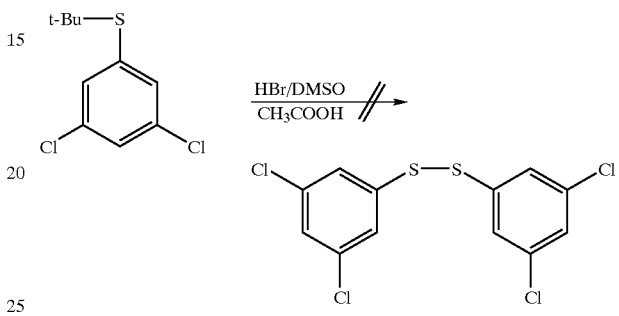

In a similar reaction vessel used in Example 1 were charged 8.9 parts of acetic acid, 4.0 parts of 3,5-dichlorophenyl t-butylsulfide and 12.6 parts of 48% hydrobromic acid. Under stirring, 1.33 parts of dimethylsulfoxide was added to the mixture while maintaining the liquid temperature to 10° C., and stirring was further continued at room temperature overnight. The solution changed to yellow color and smell of the generated dimethylsulfide was confirmed. However, the reaction hardly proceeded, and substantially the same amounts of the starting materials were recovered.

EXAMPLE 5

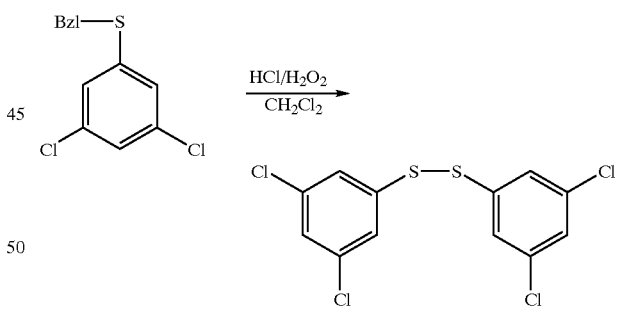

In the similar reaction vessel used in Example 1 were charged 13.3 parts of methylene chloride, 5.38 parts of 3,5-dichlorophenylbenzylsulfide and 10.1 parts of 48% hydrobromic acid. Under stirring, 2.00 parts of 34% hydrogen peroxide was added dropwise over 10 minutes while maintaining the liquid temperature to 10° C. After completion of the dropwise addition, stirring was continued for further 4 hours at the same temperature to complete the reaction.

After completion of the reaction, 13.3 parts of methylene chloride was further added to the mixture and the resulting mixture was stirred. The organic phase was collected by liquid separation, washed three times with 10.8 parts of an aqueous 10% sodium thiosulfate solution, filtered and methylene chloride was removed by distillation from the filtrate under reduced pressure. The group thus obtained was recrystallized from acetone-methanol and 1.95 parts of colorless needle crystals were obtained.

Melting point: 65° C.; $^1$H-NMR (CDCl$_3$): δ 7.33 (d, J=1.7 Hz, 4H), 7.23 (t, J=1.7 Hz, 2H).

From the results, the resulting product was confirmed to be bis(3,5-dichlorophenyl)disulfide. The yield was 55% based on the theoretical amount.

EXAMPLE 6

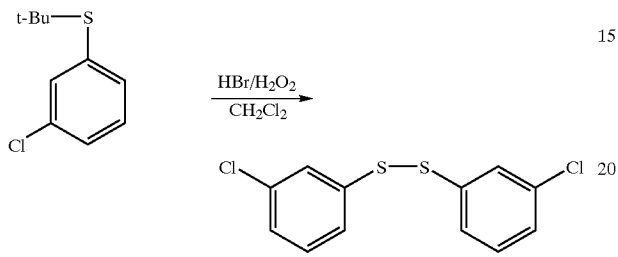

The reaction was carried out in the same manner as in Example 5 except for using 4.01 parts of 3-chlorophenyl t-butylsulfide in place of 3,5-dichlorophenylbenzylsulfide and changing the reaction time after completion of the dropwise addition to 2 hours. After completion of the reaction, from liquid separation to removal of methylene chloride by distillation were carried out in the same manner as in Example 5 and 2.78 parts of pale yellowish oily product were obtained.

$^1$H-NMR (CDCl$_3$): δ 7.47 (m, 2H), 7.35 (dt, J=2.1, 7.0 Hz, 2H), 7.22 (t, J=7.0 Hz, 2H), 7.20 (dt, J=2.1, 7.0 Hz, 2H).

From the results, the resulting product was confirmed to be bis(3-chlorophenyl)disulfide. The yield was 97% based on the theoretical amount.

EXAMPLE 7

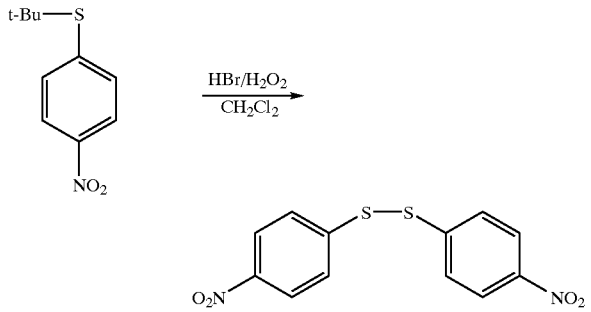

In the similar reaction vessel used in Example 1 were charged 20.0 parts of methylene chloride, 2.11 parts of 4-nitrophenyl t-butylsulfide and 5.04 parts of 48% hydrobromic acid. Under stirring, 10.0 parts of 34% hydrogen peroxide was added to the mixture over 10 minutes while maintaining the liquid temperature to 10° C. After completion of the dropwise addition, stirring was continued for further 15 minutes at the same temperature to complete the reaction.

After completion of the reaction, precipitated crystals were collected by filtration and 0.94 part of pale yellowish crystals was obtained. Moreover, the filtrate was allowed to stand, the organic phase was collected by separation and subjected to the same procedure as in Example 4 from washing with an aqueous sodium thiosulfate solution to removal of methylene chloride. The group was washed with methanol and 0.28 part of pale yellowish crystals was obtained. Melting points and NMR spectra of both of the resulting crystals accorded to each other and the both were the same compound.

Melting point: 182.5 to 183.5° C.; $^1$H-NMR (CDCl$_3$): δ 8.20 (d, J=8.9 Hz, 4H), 7.82 (t, J=8.9 Hz, 4H).

From the results, the resulting product was confirmed to be bis(4-nitrophenyl)disulfide. The yield was 79% based on the theoretical amount.

What is claimed is:

1. A process for the preparation of an aromatic disulfide represented by the formula (II):

$$Y_n-Ar-S-S-Ar-Y_n \qquad (II)$$

wherein Ar represents a hydrocarbon aromatic ring group;

Y represents a monovalent electrophilic group, and when n is 2 or more, a plural number of Y's are the same or different from each other; and n is an integer of 1 to 12, which comprises carrying out a reaction by reacting:

(A) an aromatic thioether represented by the formula (I):

$$Y_n-Ar-S-R \qquad (I)$$

wherein Y, Ar and n have the same meanings as defined above; and R represents a monovalent hydrocarbyl group selected from the group consisting of a monovalent tertiary hydrocarbyl group, a benzyl group and a monovalent secondary hydrocarbyl group derived from a, benzyl group;

with (B) at least one of the following (i) or (ii):
(i) bromine;
(ii)(a) hydrogen bromide and (b) hydrogen peroxide;
in the presence of a halogenated hydrocarbon solvent.

2. The process according to claim 1, wherein the reaction is carried out by adding dropwise bromine in the range of 0.5 to 5 mol based on 1 mol of (A) aromatic thioether.

3. The process according to claim 1, wherein the reaction is carried out by mixing hydrobromic acid with (A) aromatic thioether in the range of 1 to 10 mol per mol of (A) aromatic thioether and adding dropwise hydrogen peroxide in the range of 0.5 to 5 mol based on 1 mol of (A) aromatic thioether.

4. The process according to claim 1, wherein Ar is a benzene ring group.

5. The process according to claim 1, wherein Y is at least one electrophilic group selected from the group consisting of halogeno, nitro, nitrile, sulfone, sulfamoyl and hydrocarbylsulfonyl groups.

6. The process according to claim 5, wherein Y is chloro.

7. The process according to claim 1, wherein R is a t-butyl group.

8. The process according to claim 7, wherein the process is to obtain bis(3,5-dichlorophenyl)disulfide from 3,5-dichlorophenyl t-butyl thioether.

9. The process according to claim 1, wherein (B) is (ii) which is hydrogen bromide and hydrogen peroxide.

10. The process according to claim 1, wherein the reaction is carried out at a temperature of −30 to 60° C.

11. A process for the preparation of an aromatic disulfide represented by the formula (II):

$$Y_n\text{—Ar—S—S—Ar—}Y_n \tag{II}$$

wherein Ar represents a hydrocarbon aromatic ring group; Y represents a monovalent electrophilic group, and when n is 2 or more, a plural number of Y's are the same or different from each other; and n is an integer of 1 to 12, which comprises carrying out a reaction by reacting:

(A) an aromatic thioether represented by the formula (I):

$$Y_n\text{—Ar—S—R} \tag{I}$$

wherein Y, Ar and n have the same meanings as defined above; and R represents a monovalent hydrocarbyl group selected from the group consisting of a monovalent tertiary hydrocarbyl group, a benzyl group and a monovalent secondary hydrocarbyl group derived from a benzyl group;

with chlorine, in the presence of a catalyst in a catalytic amount of at least one of iodine and hydrogen iodide; and in the presence of a halogenated hydrocarbon solvent.

12. The process according to claim 11, wherein Ar is a benzene ring group.

13. The process according to claim 11, wherein Y is at least one electrophilic group selected from the group consisting of halogeno, nitro, nitrile, sulfone, sulfamoyl and hydrocarbylsulfonyl groups.

14. The process according to claim 13, wherein Y is chloro.

15. The process according to claim 11, wherein R is a t-butyl group.

16. The process according to claim 15, wherein the process is to obtain bis(3,5-dichlorophenyl)disulfide from 3,5-dichlorophenyl t-butyl thioether.

17. The process according to claim 11, wherein the reaction is carried out at a temperature of −30 to 60° C.

18. The process according to claim 11, wherein the chlorine is a chlorine gas in an amount of 0.5 to 5 mol based on 1 mol of (A) aromatic thioether.

19. The process according to claim 18, wherein iodine is used in the range of 0.01 to 0.1 mol based on 1 mol of (A) aromatic thioether or hydrogen iodide is used in the range of 0.02 to 0.2 mol based on 1 mol of (A) aromatic thioether as the catalyst.

20. A process for the preparation of an aromatic disulfide represented by the formula (II):

$$Y_n\text{—Ar—S—S—Ar—}Y_n \tag{II}$$

wherein Ar represents a hydrocarbon aromatic ring group; Y represents a monovalent electrophilic group, and when n is 2 or more, a plural number of Y's are the same or different from each other; and n is an integer of 1 to 12, which comprises carrying out a reaction by reacting:

(A) an aromatic thioether represented by the formula (I):

$$Y_n\text{—Ar—S—R} \tag{I}$$

wherein Y, Ar and n have the same meanings as defined above; and R represents a monovalent hydrocarbyl group selected from the group consisting of a monovalent tertiary hydrocarbyl group, a benzyl group and a monovalent secondary hydrocarbyl group derived from a benzyl group;

with (a) hydrogen chloride and (b) hydrogen peroxide, in the presence of a catalytic amount of at least one of iodine and hydrogen iodide; and in the presence of a halogenated hydrocarbon solvent.

21. The process according to claim 20, wherein Ar is a benzene ring group.

22. The process according to claim 20, wherein Y is at least one electrophilic group selected from the group consisting of halogeno, nitro, nitrile, sulfone, sulfamoyl and hydrocarbylsulfonyl groups.

23. The process according to claim 22, wherein Y is chloro.

24. The process according to claim 20, wherein R is a t-butyl group.

25. The process according to claim 24, wherein the process is to obtain bis(3,5-dichlorophenyl)disulfide from 3,5-dichlorophenyl t-butyl thioether.

26. The process according to claim 20, wherein the reaction is carried out at a temperature of −30 to 60° C.

27. The process according to claim 20, wherein the reaction is carried out by mixing hydrogen chloride with (A) aromatic thioether in the range of 1 to 10 mol based on 1 mol of (A) aromatic thioether, and dropwise adding hydrogen peroxide in the range of 0.5 to 5 mol based on 1 mole of (A) aromatic thioether, in the presence of the catalyst.

28. The process according to claim 27, wherein iodine is used in the range of 0.01 to 0.1 mol based on 1 mol of (A) aromatic thioether or hydrogen iodide is used in the range of 0.02 to 0.2 mol based on 1 mol of (A) aromatic thioether as the catalyst.

\* \* \* \* \*